United States Patent [19]

Staendeke et al.

[11] Patent Number: 4,894,469

[45] Date of Patent: Jan. 16, 1990

[54] PROCESS FOR MAKING HALOGENATED PHOSPHONOPHOSPHORIC ACID-ESTERS AND THEIR USE

[75] Inventors: Horst Staendeke, Lohmar; Werner Krause, Hürth, both of Fed. Rep. of Germany

[73] Assignee: Hoechst Aktiengesellschaft, Frankfurt am Main, Fed. Rep. of Germany

[21] Appl. No.: 128,805

[22] Filed: Dec. 4, 1987

[30] Foreign Application Priority Data

Dec. 20, 1986 [DE] Fed. Rep. of Germany ........ 3643684

[51] Int. Cl.$^4$ ............................................... C07F 9/20
[52] U.S. Cl. ..................................... 558/90; 558/115; 558/163; 524/123
[58] Field of Search .................... 558/90, 89, 115, 163; 524/123

[56] References Cited

U.S. PATENT DOCUMENTS 2,934,469 4/1960 Baker et al. .
4,407,103 3/1978 Mazour ............................. 558/90
4,407,765 10/1983 Hardy ............................... 558/163

OTHER PUBLICATIONS

Sasse, K., "Phosphorsaeurederivitate" in *Houber-Weyl: Methoden der Organischen Chemie,* Vol. XII/2, p. 352.

*Primary Examiner*—Jacqueline V. Howard

[57] ABSTRACT

Halogenated phosphonophosphoric acid esters of the general formula

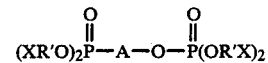

in which

X stands for a halogen

R' stands for an alkylene having from 1 to 4 carbon atoms

A stands for

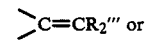

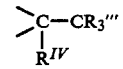

R''' stands for identical or different alkyl groups having from 1 to 4 carbon atoms, a halogen or hydrogen, and R$^{IV}$ stands for a halogen or hydrogen, are made. To this end, phosphorus (III) chloride is reacted in a first step with an alkylene oxide in the presence of a catalyst; the resulting reaction product consisting substantially of phosphorous acid trialkylesters is freed from alkylene oxide in excess and reacted in a second step with a suitable halogenoacyl halide in a molar ratio of 2:1–1.5; the resulting phosphonophosphoric acid ester is repeatedly scrubbed with water and/or an aqueous solution of ammonia and then either separated or halogenated in a third step under ultraviolet light, repeatedly scrubbed with water and/or an aqueous ammonia solution, and separated.

9 Claims, No Drawings

PROCESS FOR MAKING HALOGENATED PHOSPHONOPHOSPHORIC ACID-ESTERS AND THEIR USE

The present invention relates to a process for making phosphonophosphoric acid esters and to a novel use the compounds are put to.

It is known that phosphorous acid trialkylesters can be reacted with α-halogenocarbonyl compounds to give β-oxo-alkane-phosphonic acid dialkylesters (MICHAELIS-ARBUSOW rearrangement reaction):

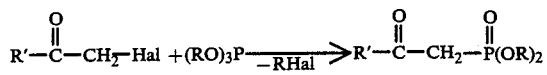

while alkyl halide is split off.

The art-recognized formation of phosphoric acid dialkylvinylesters (PERKOW-reaction)

can be deemed to take place as a competitive reaction.

By reacting a phosphorous acid trialkylester with an α-halogenoacyl halide, it is possible by combining the MICHAELIS-ARBUSOW-rearrangement reaction with the PERKOW-reaction to obtain phosphonovinylphosphoric acid esters (cf. K. Sasse, "Methoden der organischen Chemie" (HOUBEN-WEYL), volume XII/2, page 352).

It is also known from U.S. Pat. No. 2 934 469 that phosphonovinylphosphoric acid esters are readily obtainable by reacting 2 mols of a phosphorous acid trialkylester with 1 mol of an α-halogenoacyl halide, and that the said esters are useful pesticides.

We have now found that phosphorus (III) chloride can be substituted for the phosphorous acid triester formerly used as a phosphorus component in the process for making halogenated phosphonophosphoric acid esters of the general formula

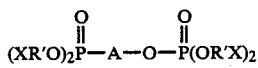

in which
X stands for a halogen,
R' stands for an alkylene having from 1 to 4 carbon atoms
A stands for

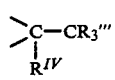

R''' stands for identical or different alkyl groups having from 1 to 4 carbon atoms, a halogen or hydrogen, and
$R^{IV}$ stands for a halogen or hydrogen, and that it unexpectedly permits the above compounds to be obtained in a so-called single stage reaction without the need to subject the triester to work-up or purifying stages. Needless to say, this permits a considerable economy of machinery and energy.

Despite this, the final product targeted is obtained in good yields and, if subjected to the scrubbing treatment of this invention, with a purity satisfactory for special uses.

The process of this invention comprises more especially: reacting phosphorus (III) chloride in a first step with alkylene oxide in the presence of a catalyst; freeing the resulting reaction product consisting substantially of phosphorous acid trialkylesters, from alkylene oxide in excess and reacting the said reaction product in a second step with a suitable halogenoacyl halide in a molar ratio of 2:1–1.5; repeatedly scrubbing the resulting phosphonophosphoric acid ester with water and/or an aqueous solution of ammonia and then either separating it or halogenating it in a third step under ultraviolet light, repeatedly scrubbing the said phosphonophosphoric acid ester with water or an aqueous ammonia solution, and separating it.

Further preferred features of the invention provide:
(a) for ethylene oxide to be used as the alkylene oxide;
(b) for chlorine or bromine to be used as the halogen;
(c) for the halogenoacyl halide used to be the chloroacetic acid chloride, the reaction product obtained in this case being the phosphoric acid-bis-(2-chloroethyl)-1-[bis-(2-chloroethyl)-phosphono]-vinylester of the formula:

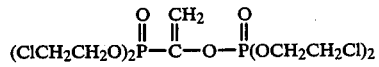

(d) for a phosphorous acid trialkylester/halogenoacyl halide-molar ratio of 2:1.1 to be maintained during the second step;
(e) for a temperature between −20° and +20° C. and reaction period between 0.5 and 5 hours to be maintained during the first step;
(f) for a temperature between 0° and 100° C. and reaction period between 0.5 and 5 hours to be maintained during the second step and third step, if any.

Water and about 10% ammonium hydroxide solution should conveniently be used alternately in the scrubbing stages of this invention; the scrubbed halogenated phosphonophosphoric acid esters are suitable for use as flame retardant compositions or components of flame retardant compositions.

A still further feature of this invention provides for the halogenated phosphonophosphoric acid esters of the general formula

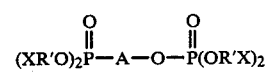

in which
X stands for a halogen
R' stands for an alkylene having from 1 to 4 carbon atoms
A stands for

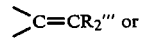

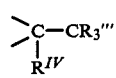

R''' stands for identical or different alkyl groups having from 1 to 4 carbon atoms, a halogen or hydrogen, and $R^{IV}$ stands for a halogen or hydrogen, to be used as agents for reducing the combustibility of combustible materials.

The flame retardant agent used for reducing the combustibility of combustible materials should preferably be selected from the halogenated phosphonophosphoric acid esters made in accordance with this invention. The products of this invention can more particularly be used for imparting flame-retardant properties to plastics materials, such as unsaturated polyesters and epoxide resins, and textiles.

The following Examples illustrate the process of this invention and the use the halogenated phosphonophosphoric acid esters are put to.

EXAMPLE 1

1. Preparation of the phosphoric acid-bis-(2-chloroethyl)-1-[bis-(2-chloroethyl)-phosphono]-vinylester 1900 g (14 mol) phosphorus (III) chloride was introduced into an agitator-provided reactor having a capacity of 5 liters, provided with a reflux condenser and thermometer, and 10 g titanium (IV) chloride was added. Next, 2000 g (45 mol) ethylene oxide was introduced over a period of 3 hours while stirring, the reaction temperature being maintained at less than 10° C. by cooling. After a post-reaction period of 1 hour at 80° C., the ethylene oxide in excess was removed under reduced pressure of about 30 millibar. 870 g (7.7 mol) chloroacetic acid chloride was added dropwise within 1.5 hour, the reaction temperature being maintained at less than 30° C. by cooling.

After a post-reaction period of 1.5 hour at 90°-100° C., the reflux condenser was replaced by a descending cooler; dichloroethane which was obtained as a secondary product was distilled off. Further volatile secondary constituents were removed under reduced pressure of about 10 millibar.

The reaction product was then scrubbed, in the sequential order indicated, with 6 liters water, 6 liters 10% ammonium hydroxide solution and again 6 liters water. The temperature was gradually increased and the water was distilled off under a pressure of about 120 millibar; residual volatile constituents were removed at a temperature of 120° C. under a pressure of 1 millibar.

After cooling, 2490 g of a colorless liquid was obtained; its analytical data were as follows:

| | | |
|---|---|---|
| density (at 25° C.) | 1.445 | g/ml |
| viscosity (at 25° C.) | 280 | mPa.s |
| refractory index (at 25° C.) | 1.4867 | |
| acid number | 1.2 | mg KOH/g |
| phosphorus content | 13.0% | P (theor. 13.6% P) |
| chlorine content | 32.1% | Cl (theor. 31.3% Cl) |

$P^{31}$—NMR-spectroscopy indicated that the product contained 85% of the compound targeted; the balance was distributed among a series of structurally related phosphoric and phosphonic acid esters.

2. Preparation of the phosphoric acid bis-(2-chloroethyl)-1-[bis-(2-chloroethyl)-phosphono]-2-chlorovinylester 1900 g (14 mol) phosphorus (III) chloride was introduced into an agitator-provided reactor having a capacity of 5 liters, provided with a reflux condenser and thermometer, and 10 g titanium (IV) chloride was added. Next, 2000 g (45 mol) ethylene oxide was introduced over a period of 3 hours while stirring, the reaction temperature being maintained at less than 10° C. by cooling. After a post-reaction period of 1 hour at 80° C., the ethylene oxide in excess was removed under reduced pressure of about 30 millibar. 1140 g (7.7 mol) dichloroacetic acid chloride was added dropwise within 1.5 hour, the reaction temperature being maintained at less than 30° C. by cooling.

After a post-reaction period of 1.5 hour at 90°-100° C., the reflux condenser was replaced by a descending cooler; dichloroethane which was obtained as a secondary product was distilled off. Further volatile secondary constituents were removed under reduced pressure of about 10 millibar.

The reaction product was then scrubbed, in the sequential order indicated, with 6 liters water, 6 liters 10% ammonium hydroxide solution and again 6 liters water. The temperature was gradually increased and the water was distilled off under a pressure of about 120 millibar; residual volatile constituents were removed at a temperature of 120° C. under a pressure of 1 millibar.

After cooling, 2980 g of a colorless liquid was obtained; its analytical data were as follows:

| | | |
|---|---|---|
| density (at 25° C.) | 1.490 | g/ml |
| viscosity (at 25° C.) | 380 | mPa.s |
| acid number | 1.5 | mg KOH/g |
| phosphorus content | 12.5% | P (theor. 12.7% P) |
| chlorine content | 37.0% | Cl (theor. 36.3% Cl) |

$P^{31}$—NMR-spectroscopy indicated that the product contained 88% of the compound targeted; the balance was distributed among a series of structurally related phosphoric and phosphonic acid esters.

3. Preparation of the phosphoric acid bis-(2-chloroethyl)-1-[bis-(2-chloroethyl)-phosphono]-1,2-dichloroethylester 1900 g (14 mol) phosphorus (III) chloride was introduced into an agitator-provided reactor having a capacity of 5 liters, provided with a reflux condenser and thermometer, and 10 g titanium (IV) chloride was added. Next, 2000 g (45 mol) ethylene oxide was introduced over a period of 3 hours while stirring, the reaction temperature being maintained at less than 10° C. by cooling. After a post-reaction period of 1 hour at 80° C., the ethylene oxide in excess was removed under reduced pressure of about 30 millibar. Next, 870 g (7.7 mol) chloroacetic acid chloride was added dropwise within 1.5 hour, the reaction temperature being maintained at less than 30° C. by cooling.

After a post-reaction period of 1.5 hour at 90°-100° C., the reflux condenser was replaced by a descending cooler; dichloroethane which was obtained as a secondary product was distilled off. Further volatile secondary constituents were removed under reduced pressure of about 10 millibar.

2000 ml tetrachloromethane was added and the reactor provided with a PHILIPS-mercury vapor lamp (HPK 125 W) having a water-cooled plunge finger.

550 g chlorine was introduced within 3 hours, and the reaction temperature was maintained at less than 10° C. by cooling. After a post reaction period of 1 hour at 50° C., the chlorine in excess was removed together with the tetrachloromethane used as a solvent. Further volatile secondary constituents were removed under reduced pressure of about 10 millibar.

The reaction product was then scrubbed, in the sequential order indicated, with 6 liters water, 6 liters 10% ammonium hydroxide solution and again 6 liters water. The temperature was gradually increased and the water was distilled off under a pressure of about 120 millibar; residual volatile constituents were removed at a temperature of 120° C. under a pressure of 1 millibar.

After cooling, 3350 g of a colorless liquid was obtained; its analytical data were as follows:

| density (at 25° C.) | 1.510 g/ml |
| viscosity (at 25° C.) | 300 mPa.s |
| acid number | 1.3 mg KOH/g |
| phosphorus content | 11.3% P (theor. 11.1% P) |
| chlorine content | 43.7% Cl (theor. 44.4% Cl) |

$P^{31}$—NMR-spectroscopy indicated that the product contained 81% of the compound targeted; the balance was distributed among a series of structurally related phosphoric and phosphonic acid esters.

4. Use of the phosphoric acid-bis-(2-chloroethyl)-1-[bis-(2-chloroethyl)-phosphono]-vinylester as an agent imparting flame-retardant properties to polyurethane foams 1000 g ®Caradol 48-2 (a registered Trade Mark of SHELL), a polyether polyol 100 g of the flame-retardant agent of Example 1

40 g water 4 g dimethylethanolamine 2 g ®Dabco 33 LV (a registered Trade Mark of HOUDRY-HÜLS), a catalyst on the basis of tertiary amines 2 g ®Desmorapid SO (a registered Trade Mark of BAYER), a catalyst on the basis of organotin compounds, and 10 g ®Tegostab B 3640 (a registered Trade Mark of GOLDSCHMIDT), a foam stabilizer on the basis of silicon compounds, were weighed into a 2-liter paperboard beaker and stirred for 1 minute using an intense stirrer. Stirring was continued (at strongly reduced velocity (rpm)) and 513 g ®Desmodur T 80, (a registered Trade Mark of BAYER), a diisocyanato-toluene, was added, and the whole was intensively mixed for 10 sec. Next, the mixture was poured immediately into a wooden mould (with the dimensions of 40×40×50 cm) provided with a paper bag. The rising or swelling period of the foam was 142 seconds.

After 5 minutes, the foamed block was placed for 15 minutes in a drying cabinet with recycle of air and allowed to remain therein for 15 minutes at 140° C.

The foam was then taken from the cabinet, stored for at least 24 hours at room temperature and tested. The following results were obtained:

Crude density: 27 kg/m³

The following values were obtained in the burning tests run in accordance with FMVSS×302 (Federal Motor Vehicle Safety Standard 302-USA-) and ASTM-D 2863-74 (oxygen-index-test USA):

| Ageing conditions | FMVSS 302-class | Oxygen index |
|---|---|---|
| unaged | self-extinguishing burning length: 21 mm | 0.21 |
| 22 hrs at 140° C. (recycle air) | self-extinguishing burning length: 16 mm | 0.22 |
| 72 hrs at 140° C. (recycle air) | self-extinguishing burning length: 12 mm | 0.23 |

The values determined for the FMVSS 302-tests as well as the numerical values determined for the oxygen-index-tests indicate that the flame-retardant effect was found to even inrease under the ageing conditions of dry heat.

We claim:

1. A process for making halogenated phosphonophosphoric acid esters of the general formula:

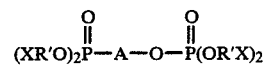

in which

X stands for a halogen

R' stands for an alkylene having from 1 to 4 carbon atoms

A stands for >C=CR₂'''

R''' stands for identical or different alkyl groups having from 1 to 4 carbon atoms, a halogen or hydrogen comprising the steps of:

(a) reacting phosphorus (III) chloride with alkylene oxide in the presence of a catalyst at a temperature between −20° and +20° C. and a reaction period between 0.5 and 5 hours;

(b) freeing the resulting reaction product consisting substantially of phosphorous acid trialkylester from alkylene oxide in excess;

(c) reacting the said reaction product with a halogenoacyl halide having from 2 to 6 carbon atoms in a molar ratio of 2:(1–1.5) at a temperature between 0° and 100° C. and a reaction period between 0.5 and 5 hours;

(d) repeatedly scrubbing the resulting phosphonophosphoric acid ester with an aqueous medium; and (e) separating said phosphonophosphoric acid ester in a distillation step.

2. A process as claimed in claim 1, wherein the alkylene oxide used is ethylene oxide.

3. A process as claimed in claim 1, wherein the halogen is chlorine or bromine.

4. A process as claimed in claim 1, wherein the halogenoacyl halide used is the chloroacetic acid chloride and the reaction product obtained is the phosphoric acid-bis-(2-chloroethyl)-1-[bis-(2-chloroethyl)-phosphono]-vinylester of the formula

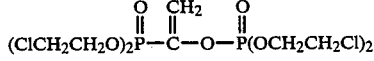

5. A process as claimed in claim 1, wherein a phosphorous acid trialkylester/halogenoacyl halide-molar ratio of 2:1.1 is maintained during said step (c).

6. A process as claimed in claim 1, wherein in step (d) the phosphonophosphoric acid ester is scrubbed with an aqueous solution of ammonia.

7. A process as claimed in claim 1 wherein in step (d) the phosphonophosphoric acid ester is scrubbed with water.

8. A process as claimed in claim 1, wherein, prior to step (e), said phosphonophosphoric acid ester is halogenated under ultraviolet light.

9. A process for reducing the combustibility of combustible materials, which comprises using a halogenated phosphonophosphoric acid ester of the general formula:

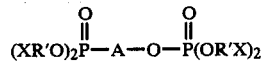

in which
X stands for a halogen
R' stands for an alkylene having from 1 to 4 carbon atoms
A stands for

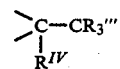

R''' stands for identical or different alkyl groups having from 1 to 4 carbon atoms, a halogen or hydrogen, and
$R^{IV}$ stands for a halogen or hydrogen.

* * * * *